(12) United States Patent
Nouvelle

(10) Patent No.: US 8,886,467 B2
(45) Date of Patent: Nov. 11, 2014

(54) PROCESS AND APPARATUS FOR PROCESSING SIGNALS

(75) Inventor: Xavier Nouvelle, Les Matelles (FR)

(73) Assignee: Schlumberger Technology Corporation, Sugar Land, TX (US)

(*) Notice: Subject to any disclaimer, the term of this patent is extended or adjusted under 35 U.S.C. 154(b) by 454 days.

(21) Appl. No.: 12/781,052

(22) Filed: May 17, 2010

(65) Prior Publication Data

US 2010/0228499 A1 Sep. 9, 2010

Related U.S. Application Data

(63) Continuation-in-part of application No. PCT/US2009/061031, filed on Oct. 16, 2009.

(30) Foreign Application Priority Data

Oct. 27, 2008 (FR) ..................... 08 05967

(51) Int. Cl.
| | | |
|---|---|---|
| *G01N 30/18* | (2006.01) | |
| *G01N 30/02* | (2006.01) | |
| *G01N 30/10* | (2006.01) | |
| *G06F 3/01* | (2006.01) | |
| *G01N 30/86* | (2006.01) | |
| *G01N 33/28* | (2006.01) | |

(52) U.S. Cl.
CPC ........ *G01N 33/2823* (2013.01); *G01N 30/8693* (2013.01); *G01N 30/8686* (2013.01)
USPC .................. 702/32; 702/22; 702/24; 702/179

(58) Field of Classification Search
USPC ........... 702/12, 24, 32, 50, 55, 100, 179, 182, 702/183; 73/152.04; 250/282; 324/324
See application file for complete search history.

(56) References Cited

U.S. PATENT DOCUMENTS

| | | | |
|---|---|---|---|
| 4,984,160 A | 1/1991 | Saint Felix et al. | |
| 6,906,320 B2 * | 6/2005 | Sachs et al. ........... | 250/282 |

(Continued)

FOREIGN PATENT DOCUMENTS

| | | |
|---|---|---|
| EP | 0437829 A1 | 7/1991 |
| EP | 0437829 B1 | 10/1994 |

OTHER PUBLICATIONS

Hu, et al., "Assessment of Chromatographic Peak Purity by Means of Artificial Neural Networks", Journal of Chromatograph A, vol. 734, 1996, pp. 259-270.

(Continued)

*Primary Examiner* — Mischita Henson
*Assistant Examiner* — Felix Suarez
(74) *Attorney, Agent, or Firm* — Rodney Warfford; Colin Wier

(57) ABSTRACT

The chemical distance between fingerprints of fluid samples from a reservoir can be determined using statistical analyses. Upon performing chromatographic analyses on fluid samples from the reservoir, certain peak height values from the chromatograms are selected, and various peak height ratios are formed using the selected peak height values. An experimental distribution of the differences between the peak height ratios is produced using two chromatograms from one of the fluid samples and a theoretical distribution of the differences of the peak height ratios are produced assuming the two chromatograms are from the one of the fluid samples. An uncertainty model of the peak height values is optimized and the parameters of the optimized uncertainty model are used to modify the theoretical distribution. The interquartile ranges of the experimental distribution and the modified theoretical distribution are determined and the chemical distance between the samples is determined using the interquartile ranges.

23 Claims, 6 Drawing Sheets

(56) References Cited

U.S. PATENT DOCUMENTS

| | | | |
|---|---|---|---|
| 6,911,822 B2* | 6/2005 | Augustine et al. | 324/324 |
| 7,277,807 B2* | 10/2007 | Dieterle et al. | 702/76 |
| 7,458,257 B2* | 12/2008 | Pop et al. | 73/152.04 |
| 2003/0197972 A1 | 10/2003 | Morris | |
| 2005/0141757 A1 | 6/2005 | Ayache et al. | |
| 2008/0031528 A1 | 2/2008 | Crombez et al. | |
| 2008/0039706 A1 | 2/2008 | Chefd'hotel et al. | |

OTHER PUBLICATIONS

Malmquist, et al., "Alignment of Chromatographic Profiles for Principal Component Analysis: A Prerequisite for Fingerprinting Methods", Journal of Chromatography A, vol. 687, 1994, pp. 71-88.

Mutihac, et al., "Mining in Chemometrics", Analytica Chimica Acta, vol. 612, Elsevier, 2008, pp. 1-18.

Shellie, et al., "Statistical Methods for Comparing Comprehensive Two-Dimensional Gas Chromatography-Time-of-Flight Mass Spectrometry Results: Metabolomic Analysis of Mouse Tissue Extracts", Journal of Chromatography A, vol. 1086, 2005, pp. 83-90.

Mexican Office Action issued in MX/A/2011/004988 on Aug. 27, 2013; 9 pages.

International Search Report & Written Opinion issued in PCT/US2009/061031 dated Dec. 15, 2009; 7 pages.

* cited by examiner

PROCESS AND APPARATUS FOR PROCESSING SIGNALS

CROSS-REFERENCE TO OTHER APPLICATIONS

This application is a continuation-in-part application claiming, under 35 U.S.C. 365(c) and 35 U.S.C. 120, priority to and the benefit of International Application No. PCT/US2009/061031, filed Oct. 16, 2009, which claims priority to and the benefit of French Patent Application No. 0805967, filed Oct. 27, 2008.

BACKGROUND

1. Technical Field

This invention concerns a process and an apparatus for processing signals. It applies in particular to the processing of signals representative of measurements made on samples to determine similarities between them. More specifically, this invention applies to the signals generated by a chromatograph to determine whether two samples of oil come from reservoirs or layers that are connected.

2. Background Art

The characterization of reservoir continuity provides information aimed at reducing the key uncertainties in an oil field whose exploitation is being contemplated, and at planning and implementing optimum reservoir development. Such characterization is therefore of great interest to the oil industry.

Reservoir characterization and reservoir continuity studies can be achieved in various ways. Some examples of characterization methods aimed at estimating reservoir compartmentalization are PVT (Pressure, Volume, Temperature) measurements, isotope analysis, GCMS (Gas Chromatography—Mass Spectrometry) techniques or FTIR (Fourier Transform Infra Red) spectroscopy, and multidimensional gas chromatography.

Among these methods, the use of oil fingerprints obtained by the analysis of gas chromatograms of crude oil is one of the quickest and least expensive. The oil fingerprint technique is relatively simple to implement. It comprises comparing various gas chromatograms of samples from different wells in an oil field. The differences between the chromatograms are used as indicators to identify possible barriers between the reservoirs covered by these wells.

Since the beginning of the 1980's, this technique, called ROF (Reservoir Oil Fingerprinting), has been widely used to estimate the connections between reservoirs or, what amounts to the same thing, the presence of flow barriers between two reservoirs. The ROF method is based on the comparison of several chromatograms obtained in the same chromatographic conditions. More specifically, it is based on the differences between the peak height ratios of the various samples analyzed.

The two peak heights used to calculate each ratio are generally selected so that they are close to one another to avoid differences due to phenomena other than reservoir compartmentalization, such as evaporation, gravitational gradients, and the immobilization of heavy components in the chromatograph. In effect, the incoherencies introduced by those mechanisms are particularly significant for components having significant retention time differences.

It is generally accepted that the accuracy of chromatographic analysis is on the order of 1 to 3%. Based on that range, differences in peak height ratios of 5 to 10% or even more cannot be attributed to analytical errors and should represent real compositional differences in crude oil composition. It is therefore customary to use a restricted selection of the most discriminating ratios to separate crude oils into meaningful groups. These groups can then be represented on star diagrams that represent the ratios in one plane to facilitate comparison.

However, this technique presents serious limitations, particularly with respect to the uncertainties as to peak height ratios: the repeatability deviations of the analysis conditions and the deterioration of the chromatographic column over time play a decisive role that is not taken into account. Furthermore, the uncertainty as to each ratio is highly dependent upon the chromatographic peaks used in that ratio. Problems such as coelutions (simultaneous detection of different components poorly separated by chromatography) or measurement noise affect the error assigned to each ratio. This problem can lead to erroneous interpretations of the chromatographic data. As proof of this, changing the list of the peak height ratios to be used in a star diagram can lead to very different results.

In addition, since only a restricted number of peak height ratios is considered, the star diagram is only a partial representation of the spatial topology of all of the peak height ratios. Furthermore, slight but numerous differences in composition between samples can have a considerable impact. This compositional variability and the subsequent difficulty of restricting the number of peak height ratios selected can lead to erroneous results.

Other interpretations using GC (Gas Chromatography) peak height ratios in statistical methods are also possible, such as ascending hierarchical classification, principal component analysis, or fuzzy logic classification. However, it is important to note that all those methods are based on relative differences in peak height ratios, the uncertainties of which are undetermined. The results obtained are therefore not expressed in absolute terms and are restricted to the comparison of crude oil samples on scales that are not the same from one series of comparisons to another.

In other words, the current state of the art does not provide a scale on which differences between samples can be universally measured. The experience acquired on past projects is therefore of little use for future projects. This is all the more troubling because there may be slight differences in composition within a single reservoir or reservoirs that are in fact connected (phenomenon of compositional gradients). Because the current state of the art does not allow the amplitudes of those phenomena to be universally quantified, specialists cannot determine whether differences between samples do or do not signify actual permeability barriers between reservoirs.

SUMMARY

The present invention is directed to a process of determining similarities between signals from a sample analysis using a single type of measurement apparatus, characterized in that it comprises a step of determining a value for each parameter of an uncertainty model related to said signals by processing homologous characteristic elements in at least two signals derived from the analysis of similar samples, and a step of determining a similarity measurement between signals based on each parameter value of the uncertainty model and of homologous characteristic elements in the signals whose similarity is being measured. The term "homologous" refers to signals that are characteristic of a specific measurement present in the various analyses, i.e., peaks of a given compound in different signals (in the specific case of chromatography, the peaks of a given compound present in different chromatograms).

As a result, the similarity measurement is directly related to the uncertainty of the measurements. It is observed that the higher the number of peak height ratios associated with the signals, the more precise the determination of the values of the uncertainty model, and the more accurate the similarity measurement. Note here that the similar samples do not necessarily come from a single initial sample. The same sample may merely be analyzed twice, or two samples may be independently taken from the same reservoir and then analyzed.

In some embodiments, during the value determination step, a mathematical uncertainty model is optimized so that it corresponds to the experimental differences between the homologous characteristic elements in the signals from similar samples.

In some embodiments, during the value determination step, a mathematical uncertainty model is optimized so that the distribution of the Student variables constructed from the model corresponds to a theoretical Student distribution with one degree of freedom of the differences between the homologous characteristic elements in the signals from similar samples.

In some embodiments, during the parameter value determination step, the parameter values minimize the quadratic distance between a theoretical cumulative distribution function and the cumulative distribution function obtained with the characteristic elements of a pair of signals from similar samples.

In some embodiments, during the similarity measurement determination step, the mean difference is determined between the distribution obtained by calculating the differences between the homologous characteristic elements in the signals whose similarity measurement is being determined and a theoretical distribution based on the parameter values.

In some embodiments, during the similarity measurement determination stage, the mean difference is determined between the distribution obtained by calculating the differences between the homologous characteristic elements in the signals whose similarity measurement is being determined and a theoretical Student distribution based the parameter values.

In some embodiments, during the similarity measurement determination stage, the mean difference is determined between the distribution obtained by calculating the difference between the homologous characteristic elements in the signals whose similarity measurement is being determined and a theoretical Gaussian distribution based on the parameter values.

In some embodiments, during the similarity measurement determination stage, a deviation between the samples is supplied based on the mean difference. It is observed that this deviation is independent of the number N of accessible ratios, independent of the sample analysis system, and global and absolute. This deviation makes it possible to create case study databases directly usable for comparisons with any new study project or any new sample analysis apparatus. In effect, since the deviations between the samples are expressed on an absolute scale, the knowledge acquired at one site can be utilized for subsequent studies. For example, for an application to an oil field exploitation project, these databases make it possible in particular to establish composition (or similarity) variation thresholds after which a barrier can be considered to exist between the reservoirs that supplied the crude oil samples.

In some embodiments, during at least one determination step, the homologous characteristic elements are peak heights present in the different signals. It is observed that this implementation method is preferentially suited to the use of a Gaussian distribution.

In some embodiments, during at least one determination step, the homologous characteristic elements are peak height ratios present in the different signals. It is observed that this embodiment is preferentially suited to the use of a Student distribution.

In some embodiments, during the analysis step, a gas chromatograph is used to supply chromatogram signals. It is therefore possible to determine the similarities between samples that can be analyzed with such a chromatograph, such as samples of crude oil.

In some embodiments, during at least one determination step, an uncertainty model described by the following equation is used:

$$(\sigma_{Hi}^{Th})^2 = (\alpha \cdot Hi + \beta)^2.$$

$\alpha$ and $\beta$ are parameters to be optimized, and $H_i$ is the normalized height of peak i. Such an uncertainty model corresponds to numerous sample analyses, such as chromatographic analyses.

The present invention is also directed to an apparatus for determining similarities of signals from a sample analysis step using a single type of measurement apparatus, characterized in that it comprises a means of determining a value for each parameter of an uncertainty model related to the signals by processing homologous characteristic elements in at least two signals from the analysis of similar samples, and a means of determining a similarity measurement between signals based on each parameter value of the uncertainty model and homologous characteristic elements in the signals whose similarity measurement is being determined. Since the advantages, objectives, and special characteristics of this apparatus are similar to those of the process according to this invention, as briefly explained above, they are not described herein.

Other advantages, objectives, and special characteristics of the present invention will become apparent from the following description and the attached claims.

It is to be understood that the drawings are to be used to understand various embodiments and/or features. The figures are not intended to unduly limit any present or future claims related to this application.

DETAILED DESCRIPTION

As explained above, this invention concerns, in general, a process and an apparatus for processing signals. It applies in particular to the processing of signals representative of measurements made on samples to determine similarities between them, as explained in relation to FIG. 1. More specifically, this invention applies to signals generated by a chromatograph to determine whether two samples of oil come from reservoirs or layers that are connected, as explained in relation to FIG. 2.

Figure 1:
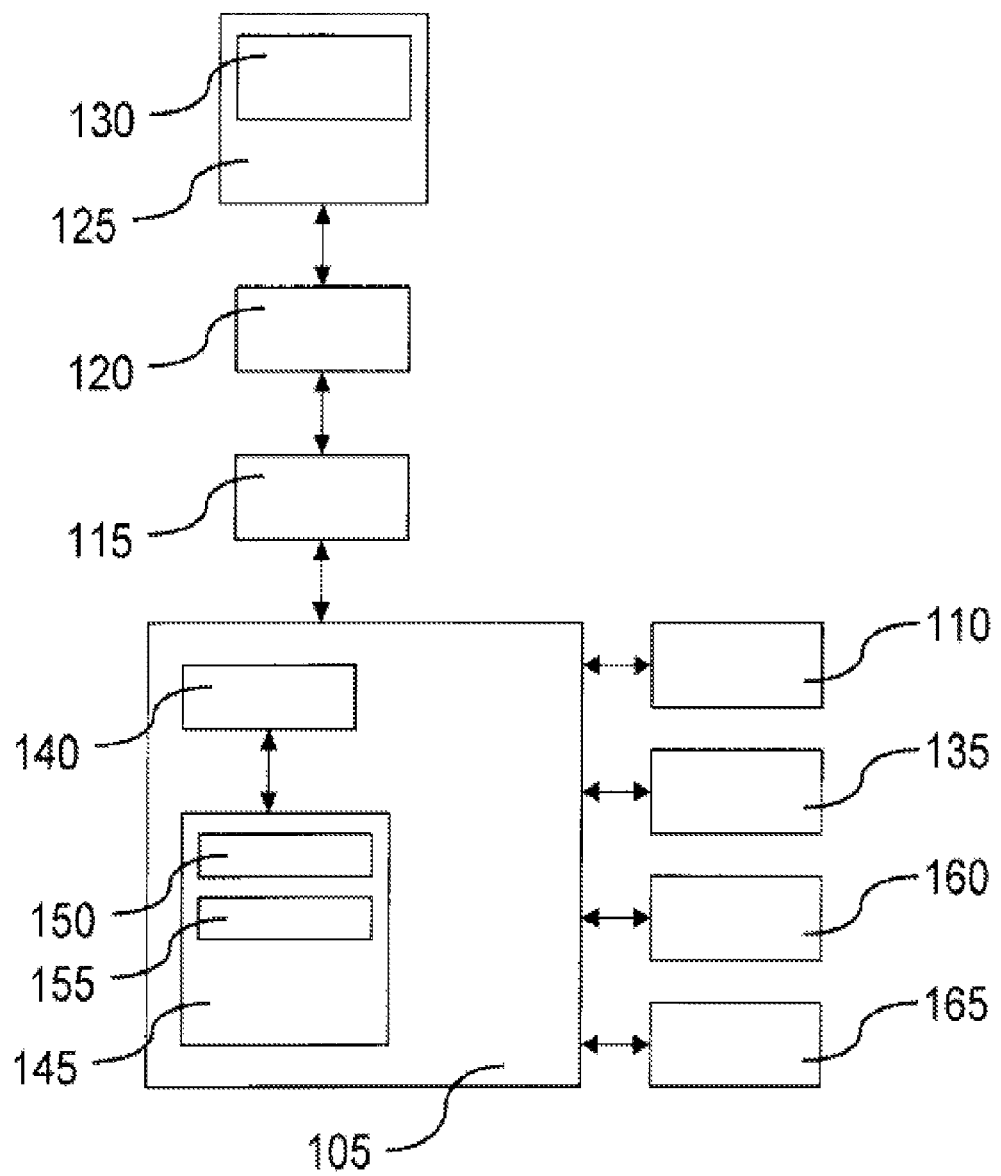
FIG. 1 schematically represents a first implementation method of a device according to this invention.

FIG. 1 shows a local terminal 105 equipped with a printer 110, a means of capturing physical quantities 135, and a means of access 115 to a network 120 to which a server 125 is connected. The server 125 is furnished with a database 130.

The local terminal 105 is, for example, a commonly used computer. The local terminal 105 controls the printing of sample similarity tables and the interpretation of such tables. The means of access 115 to the network 120 is, for example, a modem of a known type permitting access to the network 120, for example the internet. The server 125 is of a known type. The database 130 contains at least a list of similarity or deviation measurements between samples already processed using the process according to this invention, along with sample identifiers and possibly means of capturing physical quantities 135 used to analyze the samples. The terminal 105 contains software that, when run, implements the steps in the process according to this invention. The server 125 contains software that, when run, implements the steps of a similarity or deviation measurement storage and access process. Alternatively, the terminal 105 does not contain specific software but implements a web browser and a web service contained in the server 125.

The terminal 105 and/or the server 125 is adapted to determining similarities in signals from the same means of capture 135, also called "measuring device." To that end, the terminal 105 and/or the server 125 contains a means of determining a value for each parameter of an uncertainty model related to the signals by processing homologous characteristic elements in at least two signals from the analysis of similar samples, and a means of determining a similarity measurement between signals based on each parameter value of the uncertainty model and homologous characteristic elements in the signals whose similarity measurement is being determined. Those means are, for example, composed of a microprocessor 140 and memories 145 containing an operating system 150 and application software 155 containing instructions to implement the process according to this invention. Further, in a known manner, the local terminal 105 is equipped with a display screen 160 and means of control 165: for example, a keyboard and a mouse.

The following describes an implementation of this invention for processing signals from a means of capture 135 composed of a gas chromatograph adapted to produce chromatograms of crude oil samples. However, this invention is not limited to this type of means of capture, but on the contrary extends to all types of means of capturing physical quantities, such as sound, mechanical, electrical, or magnetic signals, vibrations, or images. It makes it possible to determine a level of similarities between signals from such means of capture. For example, this invention can be used to recognize or differentiate voices, pronounced words and phrases, objects present in visual or audio scenes, seismic shocks, and electromagnetic waves.

In the case of application to the oil industry, this invention uses a new statistical method for analyzing gas chromatograms, which is based on a coherent quantification of the uncertainty of peak height measurements. The quantification of the uncertainties inherent to each peak height permits a more precise differentiation. Note that it may be used in other fields, such as commingled streams allocation.

Figure 2:
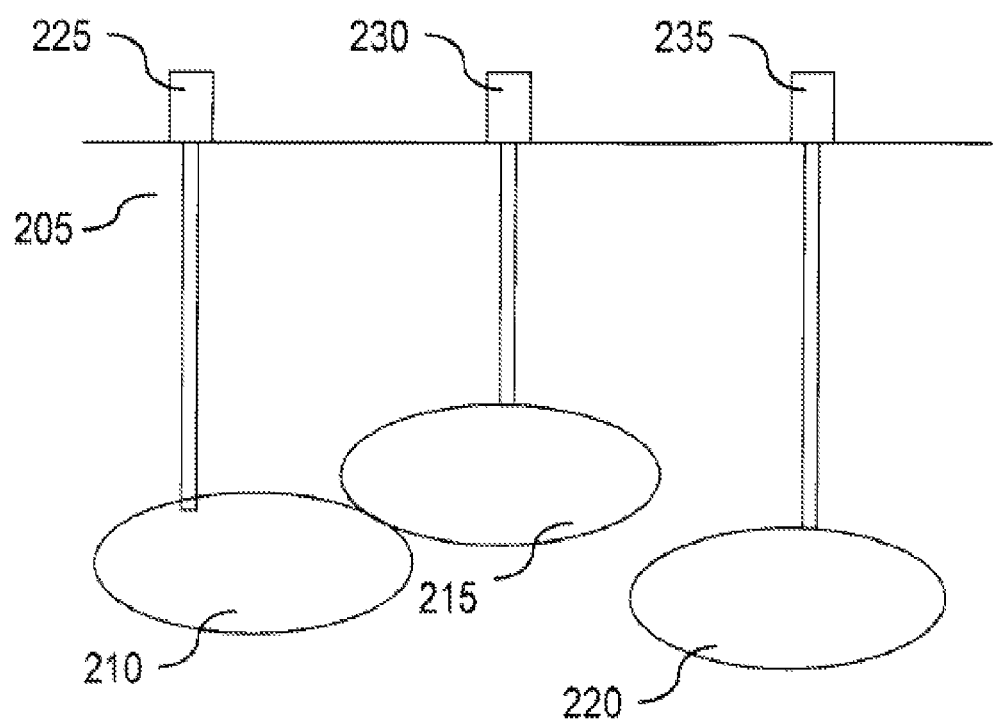
FIG. 2 schematically represents an oil field with wells.

FIG. 2 shows underground crude oil reservoirs 210, 215, and 220 in an oil field 205. Sample collection wells 225, 230, and 235 permit the collection of samples in each of the reservoirs 210, 215, and 220, respectively.

One of the problems posed for the exploitation of this oil field is the number of wells necessary to reach all the reservoirs. Correlatively, there is an effort to find reservoirs that are connected by an oil flow such as reservoirs 210 and 215 in FIG. 2, and reservoirs that are not connected. For example, reservoir 220 is not connected to reservoir 210 or to reservoir 215. The processing of gas chromatograms using the process according to this invention makes it possible to estimate the similarity of the chemical compositions of the crude oil samples collected and, accordingly, to provide a probability of connection between reservoirs.

Figure 3:
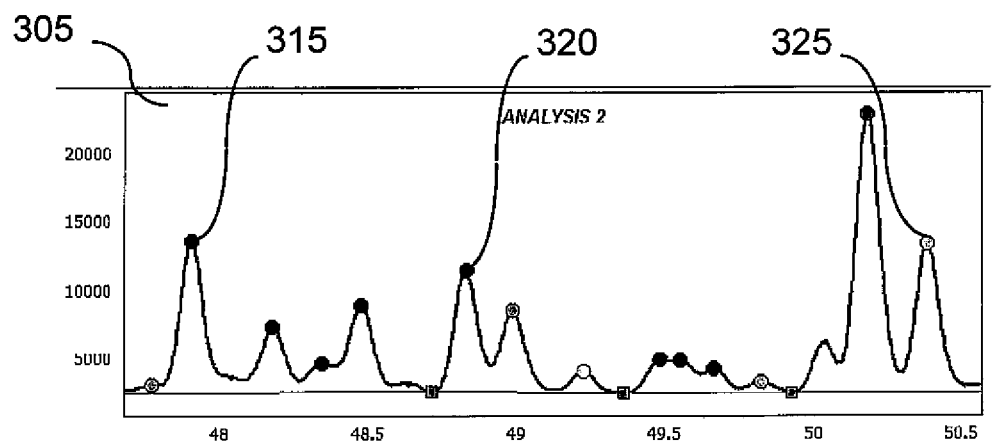
FIG. 3 schematically represents extracts from gas chromatograms of samples of crude oil.
Figure 3:
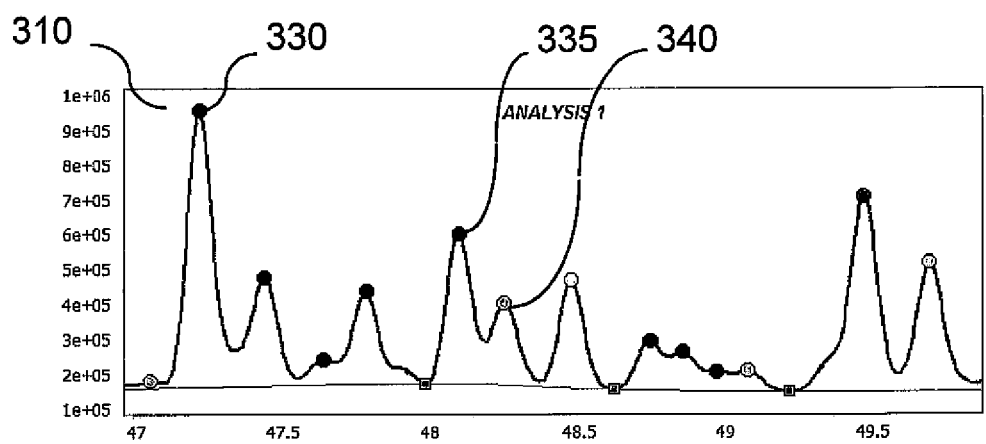

Two chromatogram extracts 305 and 310, illustrated in FIG. 3, show that each chromatogram extract contains peaks, 315 to 325, and 330 to 340, respectively. Those peaks may face one another on the two chromatograms, like peaks 315 and 330, or they may be very close to one another on the same chromatogram, like peaks 335 and 340. If the height of one peak influences the height of the other, there is coelution.

In the remaining of the description, the peak height ratios of each chromatogram are considered that chromatogram's fingerprint. Note that as many peaks as possible, even all the peaks, are used. These peaks are common to all the chromatograms, i.e., the peaks have the same Kovats index to within one chromatographic peak width.

It should be noted here that Kovats indices are relative retention values calculated so as to be independent, to the first order, of the chromatographic conditions in which the samples were analyzed. The Kovats index of a compound i is calculated using the following equation:

$$\text{KovatsID}(i) = 100(n_{C_{i-1}} + (\log_{10}(t_i) - \log_{10}(t_{C_{i-1}})) / (\log_{10}(t_{C_i}) - \log_{10}(t_{C_{i-1}})))$$

where:

KovatsID(i)=Kovats index of compound i, $n_{C_{i-1}}$=Number of carbons of the n-paraffin located just before compound i, $t_i$=Retention time of compound i, $t_{C_{i-1}}$=Retention time of the n-paraffin located just before compound i, and $t_{C_i}$=Retention time of the n-paraffin located just after compound i.

Figure 4:
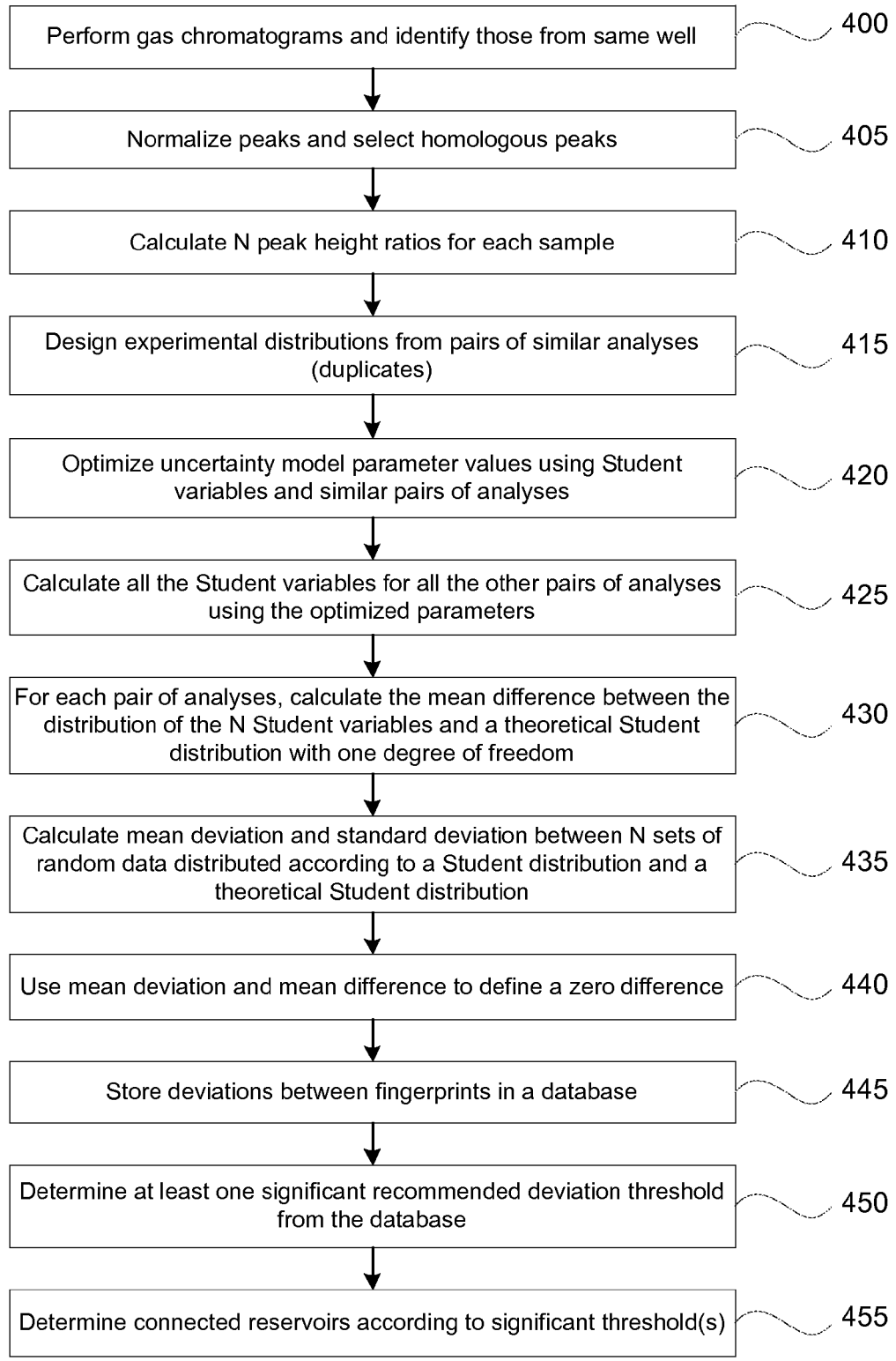
FIG. 4 represents, in the form of a logic diagram, the steps taken in a specific embodiment of the process according to this invention.

As can be seen in FIG. 4, in a specific embodiment, the first step 400 of the process comprises making a chromatogram for each sample collected, and identifying the chromatograms that involve samples from the same sample collection well.

Then, in a step 405, the peaks of the signals representing the chromatograms are normalized so as to offset the differences in injected volume of the samples in the chromatograph system, as expressed below with respect to Equation (4). In this same step 405, the homologous peaks from all the chromatograms are selected, i.e., those having the same Kovats index. This provides characteristic measurements specific to each sample in the form of the selected peak heights.

In a step 410, N ratios of these characteristic measurements are calculated for each sample. In a step 415, N Student variables are constructed from the N ratios for each pair of samples and from an uncertainty model whose parameters are to be optimized. In a step 420, from the pairs of analyses assumed to be similar and from the Student variables, the values of the parameters that optimize the uncertainty model are determined. In a step 425, all the Student variables for all the other pairs of analyses are calculated using the parameters optimized in step 420. In a step 430, for each pair of analyses, the mean difference between the distribution of the N Student variables and a theoretical Student distribution with one degree of freedom is calculated.

In a step 435, the mean deviation is established between N sets of random data distributed according to a Student distribution and a theoretical Student distribution. The standard deviation is also calculated. These values represent the expected natural variability for N variables. In a step 440, the mean deviation determined in step 435 is subtracted from the mean difference determined in step 430 so as to define a zero difference when two analyses are similar. The uncertainty as to the mean difference between two analyses is also given by the standard deviation determined in step 435.

With respect to steps 415 and 420, a mathematical model is constructed to estimate the uncertainties as to the peak height ratios between two chromatograms using the pairs of analyses pertaining to the same crude oil sample(s) and using the theoretical distribution of the expected errors (in the case of peak height ratios, Student distribution with one degree of freedom).

The uncertainty model must meet two criteria: (1) it must be sufficiently flexible so that the distribution of the Student variables (constructed from the uncertainty model) is in keeping with the Student distribution with one degree of freedom, but (2) is at the same time sufficiently general to apply to any series of analyses acquired at different times and with different devices. Numerous tests were conducted to find the best compromise between those two criteria.

With respect to the model distribution curve (Student distribution with one degree of freedom), it can be shown that the variables constructed from Equation (2) below are distributed according to a Student distribution with one degree of freedom. For this case, this model curve is preferred. However, the technique used could also be applied to more conventional measurements having a Gaussian type error, for example using peak heights instead of peak height ratios. For that case, since the variables are not in the form of ratios, one simply uses the normal distribution instead of the Student distribution with one degree of freedom.

The number of analyses to be done successively on a single batch, i.e., a single series of analyses performed with the same means of capture (in this case, the same chromatograph), is restricted for two main reasons. First, the chromatographic analysis of crude oil takes time. In addition, chromatographic data are increasingly altered as more analyses are done with the same chromatographic column. Since the number of measurements of the height of the same peak for the same fluid is very limited, the common uncertainty calculations, such as standard deviation, cannot be done with precision.

To implement the process according to this invention, the numerous peak height ratio measurements in each chromatogram are used. The Student variable t is used, which is expressed as:

$$t = \frac{(\bar{x} - \mu)}{\sigma_e / \sqrt{n}} \quad (1)$$

where:
$\bar{x}$ is the mean value of the sample for a descriptive variable x,
$\mu$ is the expectation value for variable x,
$\sigma_e$ is the standard deviation estimator for the population, and
n is the number of independent measurements in the sample.

For the example being described, the variables are the peak height ratios.

For two chromatograms representing the same crude oil, the expectation value $\mu$ is zero for each variable. In such a configuration, the Student variable t associated with each peak height ratio can be written as:

$$t_{ij} = \frac{\left(\left(\frac{H_i}{H_j}\right)_{Chromato.1} - \left(\frac{H_i}{H_j}\right)_{Chromato.2}\right)}{\sqrt{\left(\sigma_{H_i/H_j}\right)^2_{Chromato.1} + \left(\sigma_{H_i/H_j}\right)^2_{Chromato.2}}} \quad (2)$$

where $H_i$ is the normalized height of peak i.

The distribution of such a variable is known as Student distribution with one degree of freedom. When the number of variables $t_{ij}$ for each chromatogram is reasonably high, the theoretical distribution of such variables is approached if the denominator in Equation (2) is correctly estimated.

Four error factors can be determined from the measurements of the chromatograms. The first concerns the peak height in the measurement, for which it can be considered that the lower the peak height, the higher the relative error. The second refers to the phenomenon of coelution, which has a direct effect on peak height. The greater the coelution, the more a peak is modified by the contribution of neighboring peaks. The ratio between a peak height and the height of its highest valley gives a good representation of the degree of coelution. The third error factor concerns the difference in retention times of a given compound in successive analyses. In effect, if the retention time of a given compound varies from one analysis to another, the peak height measurements may be erroneously estimated due to coelution, mispositioning of the baseline, or erroneous identifications. The fourth factor involves the height of the baseline. The higher the baseline, the greater the uncertainties on the peak height measurements. All these factors were integrated into conceptual models. Each of those models was tested with different sets of data to determine its accuracy and its strength.

Since certain chromatograms come from the same crude oil sample, the cumulative distribution function, or CDF, of the t variables on each peak height ratio should follow the same trend as the theoretical Student distribution with one degree of freedom. These considerations were used to optimize the models. Specifically, the optimum values were deemed those values that minimize the quadratic distance between the theoretical CDF and the experimental CDF obtained from pairs of chromatograms from the same sample of crude oil.

The best uncertainty model is therefore the one that minimizes this criterion, but also the one that has the best potential of being universal. This latter requirement is evaluated by splitting the pairs of chromatograms of the same samples of crude oil into two groups. The first is used to optimize the parameters of the model, and the second is used to validate its universality. Universality means that the validation data (i.e., pairs of samples not used for the optimization of the uncertainty model, but acknowledged to be similar) exhibit a similarity comparable to that found for the data used for optimization. If that is not the case, the uncertainty cannot be used. For example, a dissimilarity may occur due to an excessively rapid change in the measurement system. It is therefore recommended that the same sample be analyzed at the end of the series of samples as at the beginning. Alternatively, the parameter values determined at various stages of the analysis may be interpolated.

The various simulations lead to the reduction of the number of variables in the uncertainty estimate, and the best conceptual model can be described by the following equation:

$$(\sigma_{Hi}^{Th})^2 = (\alpha \cdot Hi + \beta)^2 \quad (3)$$

in which $\alpha$ and $\beta$ are parameters to be optimized, and $H_i$ is the normalized height of peak i.

The peak heights are normalized to avoid potential effects of scale, using the following formula:

$$(H_i^{Fluid\ 1})_{Norm} = \frac{H_i^{Fluid\ 1}}{\left(\frac{1}{N_H} \sum_{j}^{N_H} H_j^{Fluid\ 1}\right)} \quad (4)$$

In effect, as illustrated in FIG. 3, peak amplitude may vary considerably from one fluid to another without increasing the relative uncertainty.

The calculation of the propagation of uncertainties can then be expressed as:

$$\sigma_{Hi/Hj}^{Th} = \frac{1}{H_j} \sqrt{(\alpha \cdot H_i + \beta)^2 + \left(\frac{H_i}{H_j}\right)^2 (\alpha \cdot H_j + \beta)^2} \quad (5)$$

which permits the transposition of the peak height uncertainties to peak height ratios uncertainties.

The distributions of the experimental (Equation 2) and theoretical Student variables are then compared to obtain an absolute measurement of the differences between the fingerprints composed of the chromatogram peak height ratios.

It is known that the characterization of the barriers between oil reservoirs is often complicated by the variability of the fluid composition in a given reservoir. Since the conventional method used to characterize compartmentalization is applied on a relative scale, and with a restriction of the peak height ratios, the composition variability due to true compartmentalization or due to thermo-gravitational (or other) effects cannot be quantified.

To solve this critical problem, the inventor has calculated an absolute deviation between the samples of crude oil. From one case to another, since the deviations are expressed on a comparable scale, the exact involvement of flow barriers and internal reservoir variability can be quantified and therefore taken into account. However, since the uncertainties on peak height ratios are not the same from one series of analyses to the next, the inventor has opted to use the Student t variable distribution curves obtained for each pair of fluids. Since each analysis is transposed in terms of t-variables, and since these variables are independent of the amplitude of the uncertainties, the mean deviation between the theoretical and experimental CDF values is expressed on a universal scale. Using the natural variability of N random variables (N being the number of peak height ratios used) distributed according to a Student distribution with one degree of freedom, the uncertainty on the evaluation of difference can also be estimated.

The simplest way to evaluate the mean deviation between the theoretical and experimental CDF values consists of applying the following formula:

$$D_{Fluid\ 1/Fluid\ 2} = \frac{1}{N} \sqrt{\sum_{i=1}^{n} (CDF_{Fluid\ 1/Fluid\ 2}(t_i) - CDF_{Theo}(t_i))^2} \quad (6)$$

in which:

$CDF_{Fluid\ 1/Fluid\ 2}(t_i)$ is the $CDF$ associated with each experimental variable $t_i$;

$CDF_{Theo}(t_i)$ is the $CDF$ associated with the same theoretical variable $t_i$; and $N$ is the number of $t$-variables.

However, this method is not sufficient when some experimental CDF values are narrower than the theoretical CDF. In such cases, the calculated deviation between the CDF values would be large, while any single-point comparison of the pair of chromatograms would be closer than expected.

This situation arises when the pairs of chromatograms used to establish the uncertainty model are more distant than others that were not used. This may occur because the CDF comparison method is sufficiently sensitive to register the gradual deterioration of the chromatograph columns during the analysis cycle of a set of crude oil samples.

The mean deviation between the experimental and theoretical CDF values is finally calculated using the following formula:

$$D_{Fluid\ 1/Fluid\ 2} = \frac{1}{n} \sum_{i=1}^{n} d_i \quad (7)$$

The values of the $d_i$ depend on the values of the variables $t_i$:

$$\text{if } t_i < 0: d_i = CDF_{Exp}(t_i) - CDF_{Theo}(t_i) \quad (8)$$

$$\text{if } t_i > 0: d_i = CDF_{Theo}(t_i) - CDF_{Exp}(t_i) \quad (9)$$

This result avoids penalizing experimental distributions that are narrower than expected according to the uncertainty model: such a case would be represented by a negative difference.

With respect to the expression of the uncertainty on the various calculations, a generator of random variables distributed according to a Student distribution with one degree of freedom was constructed. It can be used to do a simulated CDF with N random variables to calculate its differences from the theoretical CDF according to Equations (7), (8), and (9).

This process can also be repeated hundreds of times to estimate its standard deviation. This latter value corresponds to the natural variability of simulations of N variables. If the number of random variables N coincides with the number of independent ratios of the set of real data, it can be used as a reliable estimate of the uncertainty on the difference between experimental and theoretical CDF values.

Returning to FIG. 4, in a step 445, the deviations between the fingerprints are stored on an absolute scale in a database. This permits the creation of case study databases directly usable for comparisons with any new study project. In effect, since the deviations between samples are expressed on an absolute scale, the knowledge acquired on a series of analyses can be utilized for subsequent studies. Among other things, these databases make it possible to establish composition variation thresholds beyond which a barrier can be considered to exist between the reservoirs that supplied the oil samples.

In a step 450, recommended deviation thresholds can be recovered from the database beyond which samples are considered as not coming from interconnected reservoirs. In a step 455, on the basis of the recommended thresholds or thresholds specifically determined for the project, samples that come from reservoirs that are probably interconnected can be estimated based on the deviations between samples.

Table 1 below concerns two data sets consisting of several sample analyses. Each data set contains analyses of fluids from different wells but from the same oil field. Some samples were analyzed twice to construct the uncertainty model on each data set and to validate it. In Table 1, the order in which the analyses were performed has been preserved. This can be important because the quality of the peak height measurements can deteriorate as the analyses progress. For each data set, the uncertainty model was constructed using the first sample.

TABLE 1

| Data set 1 | | Data set 2 | |
|---|---|---|---|
| Analysis | Sample | Analysis | Sample |
| A1 | 1 | A1 | 1 |
| B1 | 2 | B1 | 2 |
| C1 | 3 | C1 | 3 |
| D | 4 | D1 | 4 |
| E | 5 | D2 | 4 |
| F | 6 | C2 | 3 |
| G | 7 | B2 | 2 |
| C2 | 3 | A2 | 1 |
| B2 | 2 | | |
| A2 | 1 | | |

The following describes an example of implementation of the process according to this invention. In this example, only sample 1 (analyses A1 and A2) was used to obtain the uncertainty model for each data set. The result is given in Table 2 below:

TABLE 2

| | A1 | A2 | B1 | B2 | C1 | C2 | D | E | F |
|---|---|---|---|---|---|---|---|---|---|
| A2 | −0.002 | | | | | | | | |
| B1 | 0.198 | 0.195 | | | | | | | |
| B2 | 0.196 | 0.194 | −0.023 | | | | | | |
| C1 | 0.182 | 0.181 | 0.156 | 0.157 | | | | | |
| C2 | 0.180 | 0.180 | 0.159 | 0.161 | −0.015 | | | | |
| D | 0.190 | 0.189 | 0.145 | 0.151 | 0.073 | 0.093 | | | |
| E | 0.198 | 0.197 | 0.087 | 0.099 | 0.157 | 0.160 | 0.146 | | |
| F | 0.192 | 0.191 | 0.062 | 0.063 | 0.156 | 0.157 | 0.145 | 0.087 | |
| G | 0.196 | 0.193 | 0.049 | 0.059 | 0.154 | 0.157 | 0.142 | 0.056 | −0.002 |

Analyses B1 and B2 (sample 2) and analyses C1 and C2 (sample 3) are used to validate the uncertainty model because they are not used to construct it. The analyses of these two pairs are narrower than expected, since their difference with respect to theory is slightly negative (−0.023 and −0.015, respectively). This can be explained by the order in which the analyses were done. Analyses F and G cannot be differentiated either (result of −0.002). This result means that either samples F and G come from reservoirs that are connected, or from separated reservoirs in which the crude oil has the same chemical composition (also called "false negatives").

The other analyses show significant differences in composition according to the values given in Table 2 and the 95% confidence interval (equivalent to +/−0.019). Note that to determine this value of +/−0.019 the standard deviation is multiplied by the multiplier 1.96 found in the table of Student fractiles. Such a result suggests the existence of flow barriers between the reservoirs represented by these analyses. However, the fluid composition variability in a single reservoir is actually not very well known.

As a result, the maximum threshold value beyond which the presence of a flow barrier between two reservoirs is certain may be greater than zero. The specific implementation method of the process according to this invention explained herein supplies absolute measurements between two fingerprints. It would therefore be sufficient to set this threshold a single time for a well-known project.

However, by processing the thresholds used on several past projects, a threshold to apply to a new project can be pre-estimated. As knowledge accumulates, it is also possible to determine the expected composition deviations for representatives of a given reservoir based on various parameters such as the distance between sample collection points, the nature of the reservoir rock, fractures, etc.

On the second data set, the distribution analysis results are given in Table 3 below for the 95% confidence interval (equivalent to +/−0.015). The results suggest that the differences between fingerprints can be entirely attributed to the uncertainty on the peak height measurements. It can be deduced from this that all the samples from this data set either come from the same reservoir or are "false negatives." The existence of flow barriers cannot be deduced from differences in composition.

TABLE 3

| | A1 | A2 | B1 | B2 | C1 | C2 | D1 |
|---|---|---|---|---|---|---|---|
| A2 | −0.001 | | | | | | |
| B1 | −0.013 | −0.014 | | | | | |
| B2 | −0.009 | −0.001 | −0.021 | | | | |

TABLE 3-continued

| | A1 | A2 | B1 | B2 | C1 | C2 | D1 |
|---|---|---|---|---|---|---|---|
| C1 | 0.005 | 0.011 | −0.001 | 0.006 | | | |
| C2 | 0.004 | 0.018 | −0.003 | 0.006 | −0.003 | | |
| D1 | 0.011 | 0.002 | −0.002 | 0.006 | −0.008 | −0.006 | |
| D2 | 0.001 | 0.008 | 0.002 | 0.002 | −0.013 | −0.016 | −0.005 |

The process according to this invention provides an estimate of peak height ratio uncertainty on the basis of solid theoretical knowledge, even if the number of measurements of each peak height for a given fluid is very limited.

This invention involves analyzing the distribution of the differences between two representations (in this case, chromatograms) of the same fluid (for example, the same sample), instead of focusing on the values of the peak height ratios associated with those representations. The uncertainty model constructed on two fingerprints from the same sample (in this case, crude oil) is applied to the other fingerprints made with the same equipment (in this case, the same chromatograph column), and the number of analyses made for the same data set must be sufficiently restricted to preserve the generality of the model. In the implementation method explained in Example 2 above, each sample results in a pair of analyses supplying pairs of fingerprints, only one of which was used to construct the uncertainty model.

In addition, this invention involves determining a deviation between fingerprints on an absolute scale. The distribution of variables determined for a pair of analyses is compared to the theoretical distribution obtained assuming those analyses were performed on the same sample. The mean deviation, compared to the expected natural variability, provides an absolute measurement of the differences between these two fingerprints. The inventor has determined that the uncertainties between two analyses can be used as a strong basis for estimating the actual deviation between them.

The inventor has further developed a more general analysis technique based on the consistent quantification of the uncertainty in the peak height measurements. Thus, similar to that described above, one may obtain the absolute (chemical) distances between fingerprints on a universal scale. One may also create a database of case studies that allows direct comparison with results from any new investigation. That is, the knowledge acquired from previous studies can readily be used to set a threshold of composition variability for which the conclusion that barriers/baffles are present is justified. Using this more general method, one may discriminate between samples even if the amplitude of the compositional differences is about the same as the error in the peak heights measurements. The distances between the samples do not depend on the number of peak height ratios available or on the uncertainty in the peak heights measurements. Instead, the rigorous quantification of the uncertainties in the peak height ratios allows for their subsequent use to determine chemical distances between analyses on a universal scale. By taking into account the different shortcomings of the prior art methods, one can make an accurate comparison of the chemical composition of fluids, and thus assess, for example, reservoir continuity.

As stated above, the number of analyses that can be performed on a single batch is restricted for at least two reasons. The chromatographic analyses of petroleum crude oils take time, and the chromatographic data are altered proportionally with the number of analyses performed on a single batch. Thus, the number of measurements for the same peak in the same fluid is very limited, and the usual uncertainty calculations such as standard deviation cannot be performed with precision. Because it is not possible to get a reasonable number of measurements of the same peak height ratio to quantify its uncertainty, one may instead use the high number of peak height ratios available in each chromatogram.

Peak height ratios between neighboring peaks are used to avoid differences due to phenomena other than reservoir compartmentalization: e.g., evaporation, compositional gradients, or heavy compound immobilization in the chromatographic system. Indeed, the discrepancies introduced by those mechanisms are especially noticeable for components having large molar weight differences. The ratios of neighboring peaks are called the "local composition".

From chromatograms of the same sample analyzed twice (e.g., A1 and A2 above), it is possible to determine the error distribution on a series of peak height ratios. The determined distribution typically follows a trend that depends on the uncertainties in the measurements. The peak height ratio error can be approximated using equation (10):

$$\frac{H_i^{A1}}{H_j^{A1}} - \frac{H_i^{A2}}{H_j^{A2}} = \frac{\frac{H_i^{A1}+H_i^{A2}}{2}+\text{Noise}(\sigma_H)}{\frac{H_j^{A1}+H_j^{A2}}{2}+\text{Noise}(\sigma_H)} - \frac{\frac{H_i^{A1}+H_i^{A2}}{2}+\text{Noise}(\sigma_H)}{\frac{H_j^{A1}+H_j^{A2}}{2}+\text{Noise}(\sigma_H)} \quad (10)$$

The Noise function ($\text{Noise}(\sigma_H)$) generates random numbers distributed according to a Gaussian probability density function and proportional to $\sigma_H$. That is, the Noise function is assumed to be Gaussian and its amplitude dependent on the peak height uncertainty. For that reason, the difference above (Equation 10) is different from zero, but distributed around zero. Tests carried out on various datasets have shown that the uncertainty is a constant to be optimized for each dataset of chromatograms analyzed from the same batch. The optimization makes the distribution derived from Equation (10) match, to the fullest extent possible, the experimental distribution.

Since the obtained distributions of peak height ratio differences are close to a Cauchy distribution, with heavy tails, the Euclidean distances are not particularly relevant. The differences between two chromatograms from the same sample are subject to too much variability, and, in addition, the Euclidean distance depends on the number of peak ratios available, and thus cannot constitute a universal measurement of similarity.

The distance between two samples having statistical dispersions in their distributions can, however, be measured using the interquartile range (IQR). For each pair of chromatograms, the dispersion of the distribution of their differences, if these chromatograms come from the same sample, can be characterized using the optimized uncertainty of two chromatograms of the same sample. The expected dispersion can be compared to the real dispersion, giving a consistent delineation between significant and insignificant differences. For each pair of chromatograms, the differences of peak height ratios are sorted and the median Q2 of the whole dataset is determined. The whole dataset is then divided into two sets. The first set groups all the values on one side of Q2, and the second set groups all values on the other side of Q2. The medians Q1 and Q3 are determined for each of those sets. The (experimental) IQR is the difference Q3–Q1.

The distribution of the peak height ratio differences for a pair of analyses may be compared to the distribution obtained if those analyses are from the same oil and affected by the optimized uncertainty. From the latter distribution, the IQR of threshold can be computed. It again delineates significant differences from insignificant differences, according to the uncertainty model. The experimental IQR does not depend on the number of peak height ratios available or on the uncertainty in the peak height measurements when compared to the IQR of threshold. That is, when the experimental IQR is greater than the IQR of threshold (in other words, when the differences between two chromatograms are significant), the experimental IQR does not depend on the uncertainty in the peak heights measurements. The width of the distribution is essentially due to the true differences between the chromatograms, and the error on the measurements has only a second order effect. The effects of true differences and errors on the measurements are not additive.

To illustrate, an analysis has been performed using a dataset of seven samples (A, B, C, D, E, F and G) collected from the same field. Those samples were analyzed by gas chromatography and processed as described above. Two chromatograms of samples A, B and C were acquired, but the uncertainty model was constructed using only A1 and A2, so as to evaluate the reliability when compared to samples B and C. The IQR of threshold was found to be 0.023. The results are presented in Table 4 and show the IQR for each pair of chromatograms.

TABLE 4

Calculated IQR for each pair of chromatograms

| IQR | Analysis A1 | Analysis A2 | Analysis B1 | Analysis B2 | Analysis C1 | Analysis C2 | Analysis D | Analysis E | Analysis F | Analysis G |
|---|---|---|---|---|---|---|---|---|---|---|
| Analysis A1 | 0 | | | | | | | | | |
| Analysis A2 | 0.023 | 0 | | | | | | | | |
| Analysis B1 | 0.460 | 0.460 | 0 | | | | | | | |
| Analysis B2 | 0.458 | 0.461 | 0.018 | 0 | | | | | | |
| Analysis C1 | 0.298 | 0.304 | 0.186 | 0.186 | 0 | | | | | |
| Analysis C2 | 0.290 | 0.293 | 0.189 | 0.191 | 0.020 | 0 | | | | |
| Analysts D | 0.325 | 0.338 | 0.144 | 0.150 | 0.053 | 0.066 | 0 | | | |
| Analysis E | 0.429 | 0.436 | 0.061 | 0.069 | 0.170 | 0.175 | 0.133 | 0 | | |
| Analysis F | 0.453 | 0.448 | 0.049 | 0.050 | 0.175 | 0.174 | 0.140 | 0.066 | 0 | |
| Analysis G | 0.446 | 0.449 | 0.043 | 0.047 | 0.168 | 0.178 | 0.139 | 0.047 | 0.025 | 0 |

As expected, A1 and A2, B1 and B2, and C1 and C2 are similar and validate the uncertainty model. In addition, F and G are also very close to one another. The IQR between samples F and G is 0.025.

Assuming that fluids F and G were independently sampled from the same reservoir, the effect of the sampling on the composition can be quantified as:

$$IQR_{F;G}^{Measured} = IQR_{F;G}^{Threshold} + IQR_{F;G}^{Sampling} = 0 \quad (11)$$

According to equation 11, the variability of the IQR due to the sampling would be about 0.002, which is negligible relative to the IQR of threshold.

Assuming the reservoir corresponding to analyses B1 and B2 is connected to the reservoir where F and G were sampled, one can also quantify the effect of the variability of the compositional gradients:

$$IQR_{B1B2;FG}^{Measured} = IQR^{Threshold} + IQR^{Sampling} + IQR^{Gradients} = 0 \quad (12)$$

According to Equation (12), the variability of the IQR due to compositional gradients would be 0.025, which is about the same magnitude as the IQR due to the uncertainties.

Figure 5:
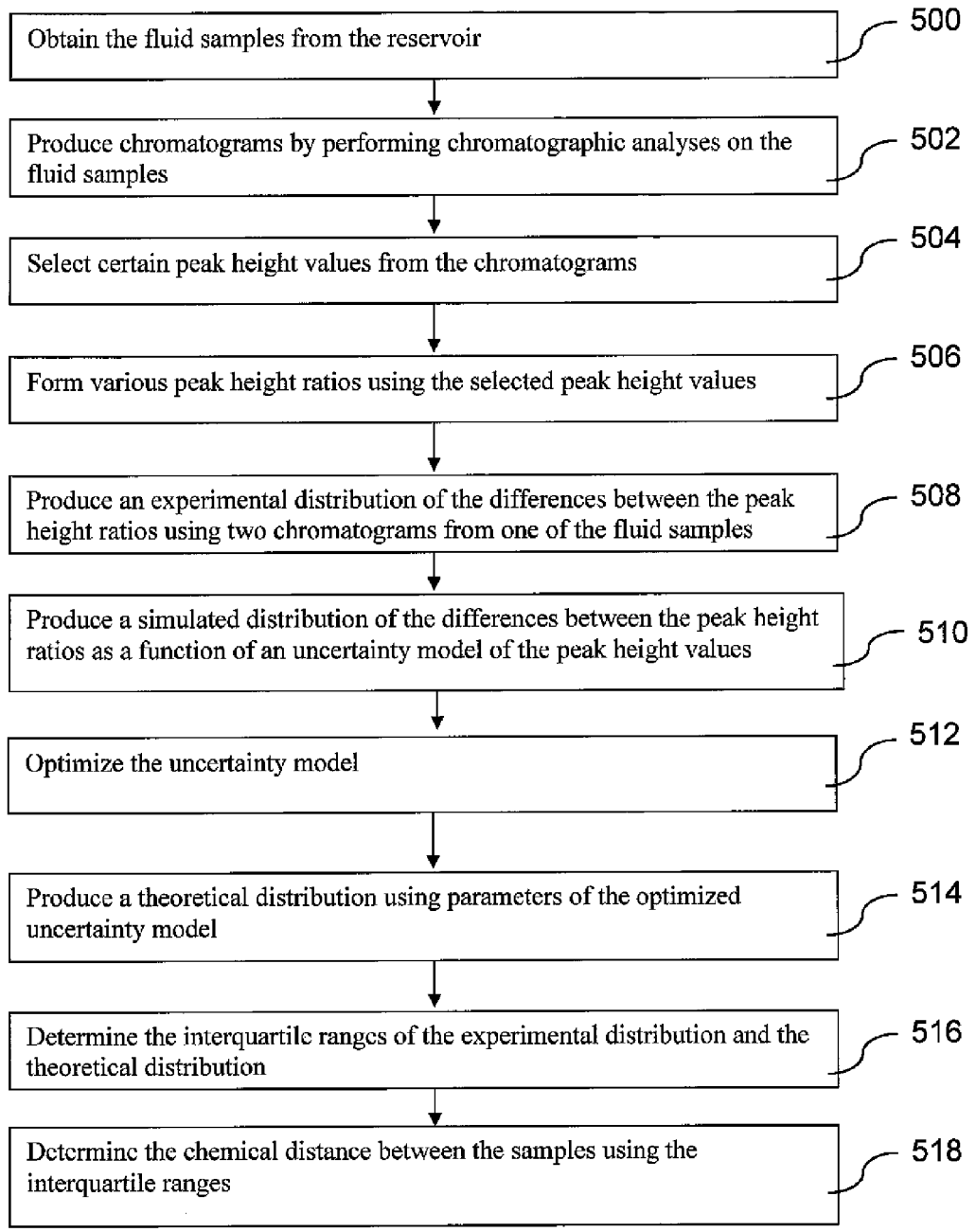
FIG. 5 represents, in the form of a logic diagram, the steps taken in a specific embodiment of the process according to this invention.

FIG. 5 shows a flowchart in which particular steps are taken in accordance with one embodiment of the present disclosure. In step 500, fluid samples are obtained from the reservoir. Chromatograms are produced by performing chromatographic analyses on the fluid samples (step 502) and certain peak height values are selected from the chromatograms (step 504). In step 506, one forms various peak height ratios using the selected peak height values. An experimental distribution of the differences between the peak height ratios is produced using two chromatograms from one of the fluid samples (step 508). Similarly, a simulated distribution of the differences between the peak height ratios as a function of an uncertainty model of the peak height values is produced (step 510). The uncertainty model of the peak height values is optimized (step 512) and the theoretical distribution is produced using parameters of the optimized uncertainty model (step 514). The interquartile ranges of the experimental distribution and the modified theoretical distribution are determined (step 516) and the chemical distance between the samples are determine using the interquartile ranges (step 518).

Figure 6:
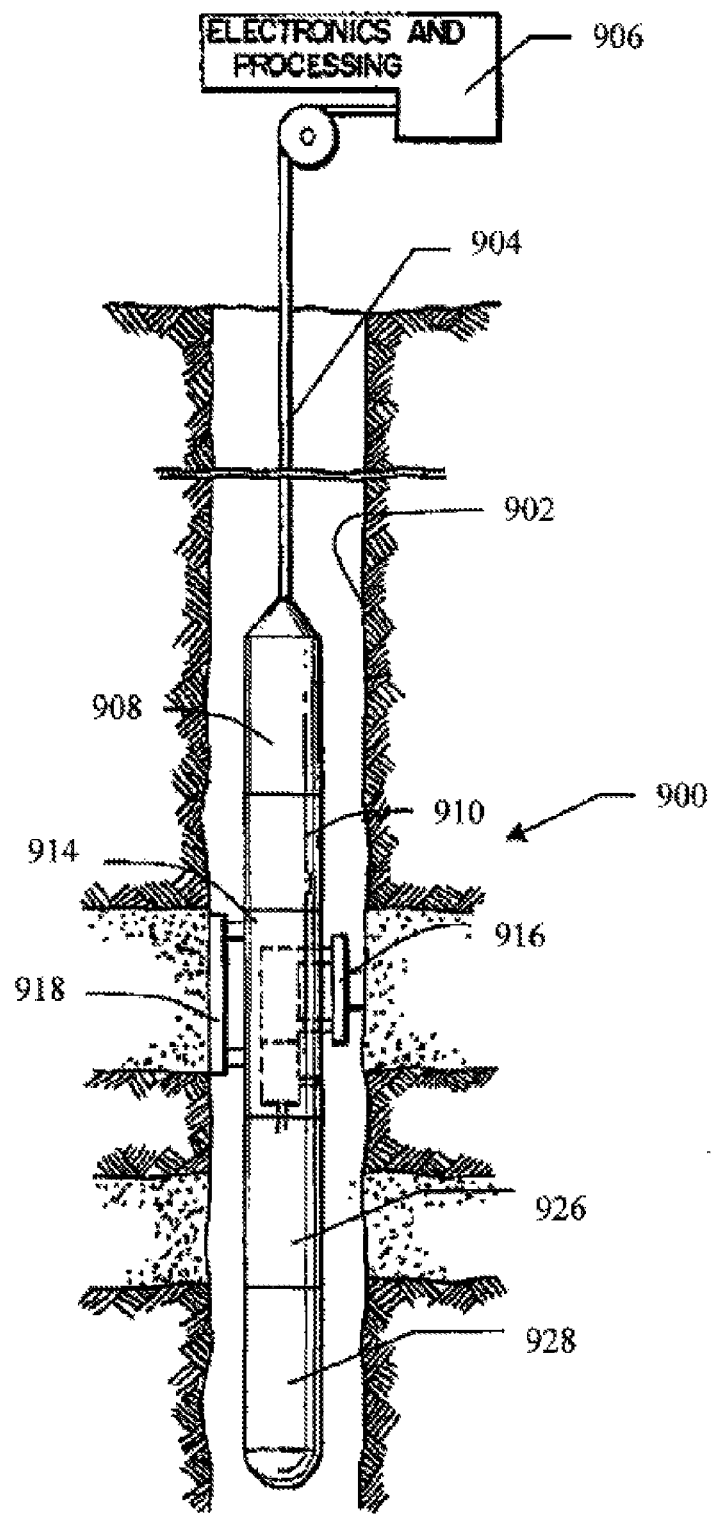
FIG. 6 is a schematic drawing showing an example wireline tool disposed in a wellbore, according to one or more aspects of the present disclosure.

Referring to FIG. 6, shown is an example wireline tool 900 in which aspects of the present disclosure may be implemented. The example wireline tool 900 is suspended in a wellbore 902 from the lower end of a multiconductor cable 904 that is spooled on a winch (not shown) at the Earth's surface. At the surface, the cable 904 is communicatively coupled to an electronics and processing system 906. The example wireline tool 900 includes an elongated body 908 that includes a formation tester 914 having a selectively extendable probe assembly 916 and a selectively extendable tool anchoring member 918 that are arranged on opposite sides of the elongated body 908. A chromatograph system 910 is also included in tool 900. Additional components (not shown) may also be included.

The extendable probe assembly 916 is configured to selectively seal off or isolate selected portions of the wall of the wellbore 902 to fluidly couple to the adjacent formation F and/or to draw fluid samples from the formation F. Accordingly, the extendable probe assembly 916 may be provided with a probe having an embedded plate. The formation fluid may be expelled through a port (not shown) or it may be sent to one or more fluid collecting chambers 926 and 928. In the illustrated example, the electronics and processing system 906 and/or a downhole control system are configured to control the extendable probe assembly 916 and/or the drawing of a fluid sample from the formation F.

While preferred embodiments have been described herein, those skilled in the art, having benefit of this disclosure, will appreciate that other embodiments are envisioned that do not depart from the inventive scope of the present application. Accordingly, the scope of the present claims or any subsequent related claims shall not be unduly limited by the description of the preferred embodiments herein.

What is claimed is:

1. A method to determine a chemical distance between fingerprints for fluid samples from a reservoir, comprising:
   obtaining the fluid samples from the reservoir using a measuring device;
   producing chromatograms by performing chromatographic analyses on the fluid samples;
   selecting, using a processor, certain peak height values from the chromatograms;
   forming various peak height ratios using the selected peak height values;

producing an experimental distribution of the differences between the peak height ratios using two chromatograms from one of the fluid samples;

producing a simulated distribution of the differences between the peak height ratios as a function of an uncertainty model of the peak height values;

optimizing the uncertainty model;

producing a theoretical distribution using parameters of the optimized uncertainty model; and determining the interquartile range of the experimental distribution and the interquartile range of the theoretical distribution; and determining the chemical distance between the samples using the interquartile ranges.

2. The method of claim 1, wherein the measuring device comprises a downhole wireline tool.

3. The method of claim 2, wherein the downhole wireline tool includes a chromatograph system.

4. The method of claim 3, wherein the producing chromatograms is performed downhole.

5. The method of claim 1, wherein the selecting certain peak height values comprises selecting from neighboring peaks.

6. The method of claim 1, wherein the producing a theoretical distribution comprises determining the error distribution on a series of peak height ratios.

7. The method of claim 1, wherein the optimizing comprises modifying parameters of the uncertainty model to shape the simulated distribution to most closely match the experimental distribution.

8. The method of claim 1, further comprising determining a chemical distance threshold between the fluid samples using the optimized uncertainty model.

9. The method of claim 1, further comprising characterizing the dispersion of the distribution of the differences between each pair of chromatograms obtained from a common sample.

10. The method of claim 9, wherein the characterizing comprises using the optimized uncertainty of two chromatograms of the common sample.

11. The method of claim 1, wherein the determined chemical distance between fingerprints is an absolute quantity measured on a universal scale.

12. The method of claim 11, further comprising maintaining a database of the determined absolute chemical distances between fingerprints.

13. The method of claim 12, further comprising using the database to set a threshold of composition variability.

14. A system to determine a chemical distance between fingerprints for fluid samples from a reservoir, comprising:

a computer system comprising a central processing unit, an input device, and an output device;

input data that can be read by the input device, the input data comprising two or more chromatograms characterizing one or more of the fluid samples; and a computer program that can be run on the central processing unit to:

select certain peak height values from the chromatograms;

form various peak height ratios using the selected peak height values;

produce an experimental distribution of the differences between the peak height ratios using two chromatograms from one of the fluid samples;

produce a simulated distribution of the differences between the peak height ratios as a function of an uncertainty model of the peak height values;

optimize the uncertainty model;

produce a theoretical distribution using parameters of the optimized uncertainty model;

determine the interquartile range of the experimental distribution and the interquartile range of the theoretical distribution;

determine the chemical distance between the samples using the interquartile ranges; and output the determined chemical distance to the output device.

15. The system of claim 14, wherein the experimental interquartile range is independent of the number of peak height ratios and an uncertainty in the peak height values.

16. The system of claim 14, wherein the theoretical interquartile range delineates significant differences from insignificant differences between the two chromatograms from the one of the fluid samples.

17. The system of claim 14, wherein the computer program further comprises evaluating the accuracy of the theoretical interquartile range by comparing it to one or more interquartile ranges for other chromatogram pairs obtained from common samples.

18. The system of claim 14, wherein the computer program further comprises validating the accuracy of the uncertainty model by comparing one or more interquartile ranges for other chromatogram pairs obtained from common samples.

19. A non-transitory computer-readable medium having a set of computer-readable instructions encoded thereon that, when executed, perform acts comprising:

accepting input data obtained from a chromatograph system, the input data comprising two or more chromatograms characterizing one or more fluid samples;

selecting certain peak height values from the chromatograms;

forming various peak height ratios using the selected peak height values;

producing an experimental distribution of the differences between the peak height ratios using two chromatograms from one of the fluid samples;

producing a simulated distribution of the differences between the peak height ratios as a function of an uncertainty model of the peak height values;

optimizing the uncertainty model;

producing a theoretical distribution using parameters of the optimized uncertainty model;

determining the interquartile range of the experimental distribution and the interquartile range of the theoretical distribution;

determining a chemical distance between the samples using the interquartile ranges; and outputting the determined chemical distance to an output device.

20. The computer-readable medium of claim 19 having a set of computer-readable instructions encoded thereon that, when executed, perform acts further comprising determining the effect of variability of compositional gradients and/or determining the effect of sampling on the composition of one or more of the samples.

21. The computer-readable medium of claim 19, wherein the determined chemical distance is an absolute quantity measured on a universal scale.

22. The computer-readable medium of claim 21 having a set of computer-readable instructions encoded thereon that, when executed, perform acts further comprising maintaining a database of the determined chemical distances between the samples.

23. The computer-readable medium of claim 22 having a set of computer-readable instructions encoded thereon that, when executed, perform acts further comprising using the database to set a threshold of composition variability.

* * * * *